United States Patent [19]

Jordan et al.

[11] Patent Number: 4,780,266
[45] Date of Patent: Oct. 25, 1988

[54] METHOD FOR DETECTING DRILLING FLUID IN THE ANNULUS OF A CASED WELLBORE

[75] Inventors: Mark E. Jordan, Houston; Richard C. Haut, Missouri City; William E. Kline, Houston, all of Tex.

[73] Assignee: Exxon Production Research Company, Houston, Tex.

[21] Appl. No.: 944,723

[22] Filed: Dec. 22, 1986

[51] Int. Cl.⁴ .............................. G01V 5/00
[52] U.S. Cl. .................... 376/162; 376/159; 376/160; 376/167; 250/254; 250/270; 166/250
[58] Field of Search ............... 376/160–162, 376/159, 167; 166/336, 250, 312; 250/254, 270

[56] References Cited

U.S. PATENT DOCUMENTS

| | | | |
|---|---|---|---|
| 2,451,472 | 10/1948 | Coggeshall | 166/22 |
| 2,451,520 | 10/1948 | Teplitz | 166/22 |
| 2,484,422 | 10/1949 | Muskat et al. | 250/83.6 |
| 3,019,341 | 1/1962 | Monaghan | 250/106 |
| 3,115,576 | 12/1963 | Rickard | 250/254 |
| 3,838,279 | 9/1974 | Schultz et al. | 250/270 |
| 3,973,626 | 8/1976 | Miles | 166/250 |
| 4,051,368 | 9/1977 | Arnold et al. | 376/162 |
| 4,474,240 | 10/1984 | Oliver, Jr. et al. | 166/312 |
| 4,524,272 | 6/1985 | Paap et al. | 250/270 |
| 4,600,838 | 7/1986 | Steinman | 250/270 |

*Primary Examiner*—Harvey E. Behrend
*Attorney, Agent, or Firm*—Richard F. Phillips

[57] ABSTRACT

A method for logging a cased well to determine the quantity and location of any barite weighted drilling fluid in the annulus between the casing and the wall of the wellbore. A tool assembly having a neutron generator and a gamma scintillation detector is used to log the zone of interest. The neutrons introduced into the well by the neutron generator convert a portion of the barium-138 in the drilling fluid to barium-137m. The magnitude of the gamma photon peak characteristic of the decay of barium-137 is used to identify the quantity of drilling fluid present in the annulus as a function of depth. This method is especially useful identifying the existence of channels in a cemented wellbore annulus.

6 Claims, 1 Drawing Sheet

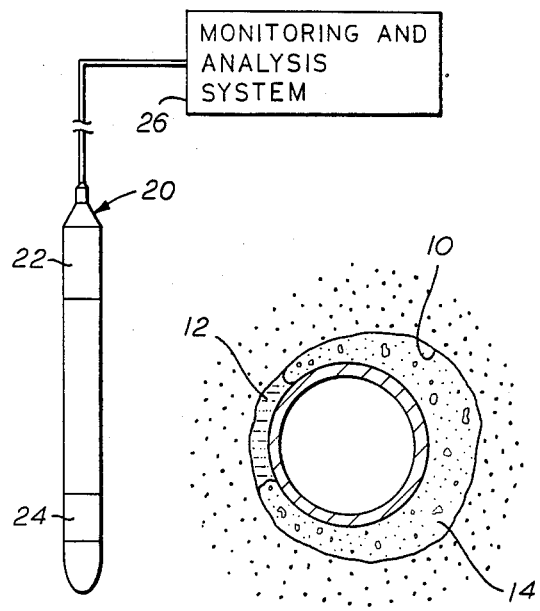
FIG. 2    FIG. 1
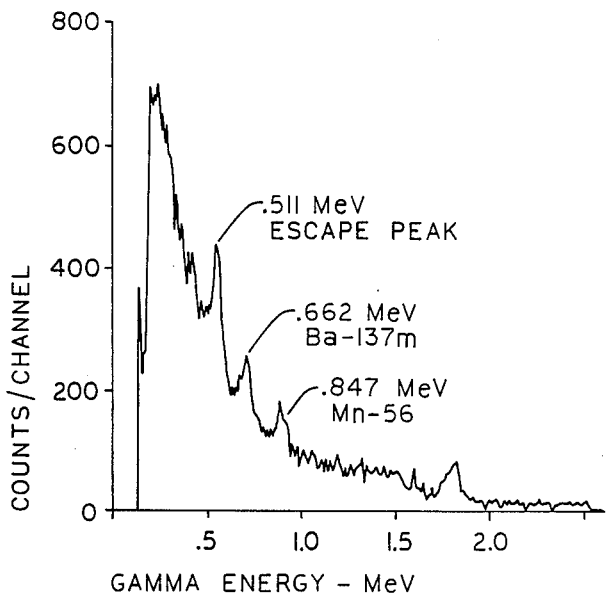
FIG. 3
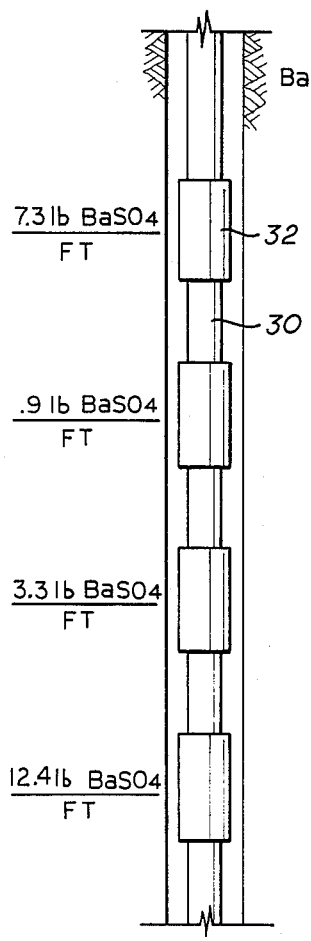
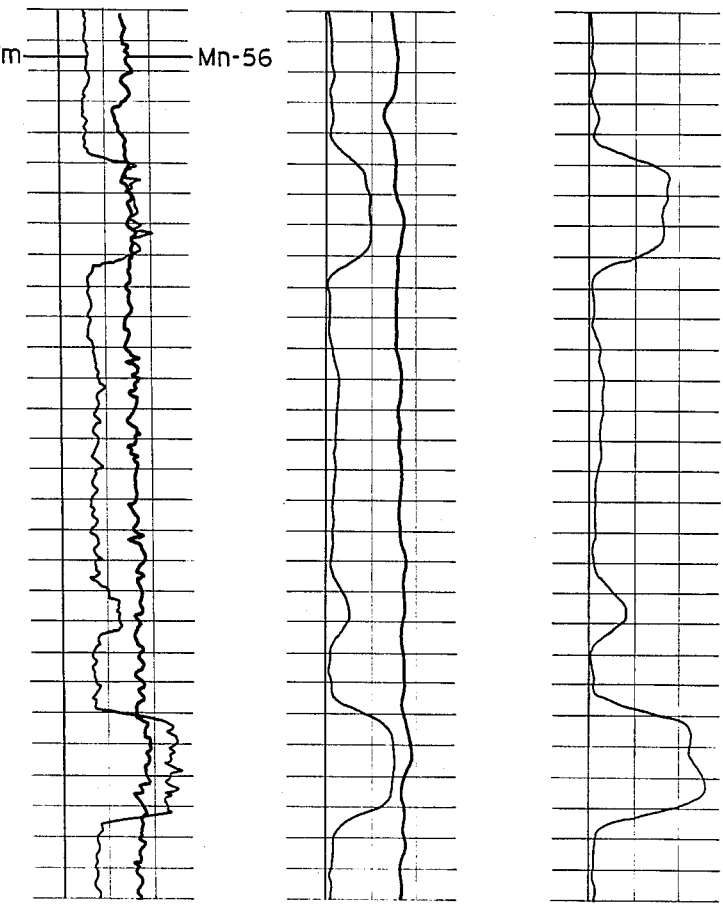
FIG. 4    FIG. 5A    FIG. 5B    FIG. 5C

METHOD FOR DETECTING DRILLING FLUID IN THE ANNULUS OF A CASED WELLBORE

TECHNICAL FIELD

The present invention relates generally to methods for completing wells. More specifically, the present invention concerns a method for detecting drilling fluid remaining in the annulus of a cased wellbore following the completion of a cementing operation.

BACKGROUND OF THE INVENTION

In the drilling of oil and gas wells it is common practice to case and cement the wellbore. This operation is typically conducted in several stages. An initial section of the well is drilled with a large diameter bit. A large diameter tubular casing is then set within this initial section of the well. Cement is then pumped through the bottom of the casing under sufficient pressure to cause it to flow upward and fill the annulus defined by the wellbore and the casing. As the cement is pumped, it displaces to the surface of the well the drilling fluid which fills the annulus at the time the casing is set. After the cement cures, a smaller diameter drill bit is passed through the first section of the casing and a second section of the well is drilled, cased and cemented. This process continues until the desired depth is reached.

A principal reason for casing and cementing a well is to establish a seal which prevents fluid communication among the various rock strata traversed by the wellbore. Occasionally, portions of the drilling fluid within the annulus are bypassed in the cementing operation. This bypassed drilling fluid most typically takes the form of channels extending a considerable distance along the annulus. This condition is called "channeling." FIG. 1 shows a cross-section of a cased borehole 10 in which channeling 12 has occurred in the cemented annulus 14. Channeling has the effect of establishing pathways along the annulus through which fluids can pass. This can result in the loss of hydrocarbons to "thief" strata; permit the production of unwanted fluids; decrease the effectiveness of acidizing, formation fracturing and other reservoir stimulation treatments; and can prevent injected drive fluids from efficiently displacing hydrocarbons in enhanced oil recovery operations. In many instances channeling, if uncorrected, can render a well worthless.

Channeling and similar cementing problems are typically corrected by a remedial cementing operation known as "squeeze cementing." In squeeze cementing, the casing is perforated at the location of the channel and cement is forced through the perforations into the channel under high pressure. The fluid within the channel is displaced into the formation by the cement. Though squeeze cementing is generally not expensive to perform, the delays in completing a well owing to the need for remedial cementing often result in significant economic loss.

It is common practice to perform a logging operation known as a "cement bond log" on newly cemented sections of a well to determine the adequacy of the cement job. Where the cement bond log indicates that channeling may have occurred, the driller must determine whether remedial cementing should be conducted. This determination is complicated by the fact that the interpretation of cement bond logs is an inexact science. An indication of a cementing problem on a cement bond log could be the result of channeling, which can be corrected by remedial cementing, or could be the result of defective cement, which generally cannot be corrected by remedial cementing.

It would be desirable were there a method for examining regions of a cased wellbore which are suspected to have an imperfect cement seal to conclusively determine whether channeling has occurred and, if so, the size of the channel. Several methods have been proposed for this; however, none are commercially available.

U.S. Pat. No. 2,451,472, issued Oct. 19, 1948, teaches the use of a drilling fluid containing a radioactive tracer for the purpose of permitting an accurate determination of the location and magnitude of channels. After the cementing operation, a gamma log of the well is conducted to detect the presence of any remaining drilling fluid. Though this method is accurate and inexpensive, the required use of significant amounts of radioactive material renders it impractical for most applications.

U.S. Pat. No. 2,451,520, issued Oct. 19, 1948, teaches a channeling detection method in which critical intervals of a cased wellbore (e.g. those near hydrocarbon bearing formations) are perforated and a liquid doped with a radioactive tracer is pumped through the perforations. The radioactive tracer will fill any channels, which can then be detected by subsequent gamma logging. Though this method yields accurate results, it is undesirable due to the expense of the perforating and injection operations required.

It would be desirable to develop a method for establishing the location and quantity of bypassed drilling fluid in a cased wellbore quickly and accurately without the need for injecting radioactive tracers into the well or drilling fluid.

SUMMARY OF THE INVENTION

The present invention is directed to a method for detecting barite weighted drilling fluid in the annulus of a wellbore. In the preferred embodiment, the present invention is practiced with a logging tool assembly including a high energy neutron source and a gamma photon scintillation detector. As the logging tool is passed through the cased wellbore, a population of high energy neutrons is introduced into the annulus. A portion of the barium within the drilling fluid is converted to Barium-137m, which decays to Barium-137. The gamma scintillation detector, in conjunction with a surface analysis system, monitors the gamma flux resulting from Barium-137m decay. From this, a log of the relative abundance of drilling fluid as a function of depth is developed.

By use of a surface calibration of the logging tool used in the practice of the present invention, the precise quantity of drilling fluid present at any given location within the wellbore can be determined. The effects of variations in logging speed and changes in the output of the neutron source can be corrected by using the observed decay rate of Manganese-56, generated by interactions between the high energy neutrons and the Iron-56 within the casing, as an activity monitor.

A preferred application of the present invention is to monitor a newly cemented section of a well for channeling. This invention is particularly useful in investigating those sections of a well which appear from a cement bond log to have been imperfectly cemented.

BRIEF DESCRIPTION OF THE DRAWINGS

For a better understanding of the present invention reference may be had to the accompanying drawings, in which:

FIG. 1 is a cross-section of a cased, cemented wellbore illustrating the presence of drilling fluid bypassed during the primary cementing process;

FIG. 2 is a schematic illustration of a logging tool assembly suitable for use in the practice of the present invention;

FIG. 3 is a gamma spectrum obtained in logging a test well having an annulus partially filled with a barite weighted drilling fluid;

FIG. 4 shows the casing-canister configuration used in testing the present invention; and FIGS. 5a–5c shows the data obtained in testing the present invention.

These figures are not intended as a definition of the invention, but are provided solely for the purpose of illustrating certain aspects of the preferred embodiment of the invention described below.

DESCRIPTION OF THE PREFERRED EMBODIMENTS

The present invention concerns a method for logging a cased well to determine the amount of drilling fluid present in the annulus between the well casing and the walls of the borehole. This method is particularly useful in determining the location and quantity of drilling fluid that may have been bypassed in the cementing of oil and gas wells. However, the present invention has other applications, such as measuring mud cake thickness in a well. To the extent the following description of the invention is specific to the evaluation of a well cementing operation, this is by way of example rather than limitation.

We have found that barite weighted drilling fluid in the annulus of a cased well can be detected by introducing a population of very high energy neutrons into the casing and then passing a gamma photon detector through the casing to detect the presence of a gamma peak centered at 0.662 MeV. Upon exposing the barite weighted drilling fluid to high energy neutrons, a portion of the barium is converted to $Ba^{137m}$ through the reaction $Ba^{138}(n,2n)Ba^{137m}$. A 0.662 MeV gamma photon is then released in the subsequent gamma decay of $Ba^{137m}$. The half life of $Ba^{137m}$ is 2.6 minutes. The cross-section for the $Ba^{138}(n,2n)Ba^{137m}$ reaction is approximately $1.1\pm0.1$ barns at a neutron energy of 14.8 MeV and drops to zero at a neutron energy of about 10 MeV. Preferably, a 14 MeV neutron generator is used to establish the neutron population causing the production of $Ba^{137m}$ from the barite weighted drilling fluid. Due to the high neutron energy required for the generation of $Ba^{137m}$, most isotopic neutron sources cannot be used in the practice of this invention.

FIG. 2 illustrates a simple logging tool 20 suitable for use in the practice of the present invention. The logging tool 20 includes a neutron generator 22 positioned above a gamma scintillation detector 24. A surface monitoring and analysis system 26 is provided to monitor the position of the logging tool 20 and to continuously record the gamma spectrum observed by the gamma detector 24. FIG. 3 illustrates a gamma spectrum obtained using such a logging tool at one location in a cased test well having an annulus filled with barite weighted drilling fluid. The 0.662 MeV $Ba^{137m}$ decay peak is readily apparent.

In the practice of the present invention, the logging tool 20 would be operated upward over the interval of interest within the well to obtain a record of the gross magnitude of the $Ba^{137m}$ peak as a function of depth. Assuming a constant logging speed and neutron output, the magnitude of the net $Ba^{137m}$ peak at any location within the casing is directly proportional to the quantity of barite in the annulus at that location. The magnitude of the net $Ba^{137m}$ peak can be plotted as a function of depth to yield a log of the relative bypassed drilling fluid content of the annulus. Regions of high $Ba^{137m}$ activity on the log are indicative of channeling in the cemented annulus.

A quantitative measure of the amount of drilling fluid present in the annulus can be established by calibrating the $Ba^{137m}$ response of the logging tool 20. This is accomplished by preparing a test cased borehole in which the annulus is filled with weighted drilling mud having a known concentration of barium. The test borehole is logged with the logging tool 20 at the logging rate used in logging actual wells to establish an observed $Ba^{137m}$ peak corresponding to the known barium concentration in the annulus. It is anticipated that in commercial use of the method of the present invention, a test response of the logging tool 20 will be established for a number of different borehole and casing size combinations. The resulting calibration data will be maintained in the monitoring and analysis system 26, which will be adapted to convert the raw $Ba^{137m}$ activity data obtained from the well of interest into a quantitative well log giving the volume fraction of drilling fluid within the annulus as a function of depth. While the amount of barite detected at a given location can generally be directly related to the quantity of drilling fluid at that location, those skilled in the art will recognize that this is not universally the case. For example, a thick mudcake may result in sufficient barite accumulation at a section of the wellbore to cause a false indication of channeling at that location. This can generally be avoided by interpreting the $Ba^{137m}$ log in conjunction with open hole logs giving the mud cake thickness.

Changes in the operating conditions of the logging tool can introduce error into the determination of the magnitude of the $Ba^{137m}$ peak. For example, variations in the detector efficiency, neutron output, logging speed, etc., will all affect the measurement. We have discovered that these sources of error can readily be eliminated by normalizing the raw $Ba^{137m}$ data to the observed 0.847 MeV gamma flux of $Mn^{56}$, which serves as a nearly ideal activity monitor. $Mn^{56}$ is generated through the reaction $Fe^{56}(n,p)\ Mn^{56}$ occurring as a result of the presence of iron in the casing. This reaction has a cross section of about 0.1 barns at a neutron energy of 14 MeV. The 0.847 MeV peak of $Mn^{56}$ decay can be seen in FIG. 3. The iron content per unit length of the casing is, of course, substantially constant over the interval to be logged—the only exception being the increased iron in the casing joints, which typically occur every 40 feet (12.2 meters). Accordingly, assuming a constant logging speed, neutron flux and detection efficiency, the magnitude of the net $Mn^{56}$ peak should be constant, save at the casing joints. Any variation in the magnitude of this peak represents some change in neutron output, logging speed, etc. which will result in a corresponding change in the magnitude of the $Ba^{137m}$ peak. To eliminate the effect of these variations in the logging conditions, the magnitude of the net $Mn^{56}$ peak is used as an activity monitor to normalize the $Ba^{137m}$ peak.

An experiment was conducted to test the present invention. A string of 5.5 inch (14.0 cm) O.D. casing was set into a test borehole. Four 7⅜ inch (19.4 cm) O.D. annular canisters 32 were secured around the casing 30 in the configuration shown in FIG. 4. The canisters 32 were each 7 feet (2.1 meters) long and were secured to the casing 30 on 12 foot (3.6 meter) centers. Each canister 32 was filled with a fluid containing a known concentration of barite. The casing was filled with water. The well was then logged using a Cyclic Activation Tool manufactured by Dresser Industries, Inc. of Houston, Texas. This tool includes a 14 MeV deuterium-tritium neutron generator having a 100 hz duty cycle. The neutron generator operates at 4 kHz for the first 4 milliseconds of each cycle and is off during the remaining 6 milliseconds of each cycle. The tool also includes two cesium-iodide gamma scintillation detectors, spaced 39 and 52 inches (99 and 132 cm) below the neutron generator. The output of the detectors is recorded only in the last several milliseconds of each 6 millisecond period when the neutron generator is off. This avoids spectrum cluttering resulting from gamma radiation resulting from neutron capture and inelastic neutron scattering interactions.

FIG. 5A is a log giving as a function of well depth the gross magnitude of the $Ba^{137m}$ and $Mn^{56}$ peaks obtained from the far detector of the Cyclic Activation Tool. FIG. 5B shows this data following the application of a digital filter and background correction to establish the net magnitude of the $Ba^{137m}$ peak. FIG. 5C shows the filtered net $Ba^{137m}$ peak normalized based on changes in the $Mn^{56}$ peak. Of the four canisters, only that with the lowest Barite concentration, 0.91 lb $BaSO_4$/ft (1.4 kg/m), approaches the detection limit on the log. The remaining three barite bearing canisters are clearly indicated by $Ba^{137m}$ activity well above background. This would appear to indicate that the limit of detectability for this method using the Cyclic Activation Tool is a channel having a cross section sufficient to yield a Barite density of about 1 lb/ft (1.5 kg/m). FIG. 5 appears to indicate that the second canister from the bottom is only partially filled. It is believed that this was the result of a leak in the canister.

The sensitivity of the method could be greatly increased by use of a germanium crystal detector or other solid state detector. The great energy resolution of such detectors results in much greater net peak to background ratios. The source-detector spacing could be adjusted to optimize the net $Ba^{137m}$ peak to background ratio for typical logging speeds. Those skilled in the art will recognize a number of other possible improvements to the present invention.

It is anticipated that in actual practice, the $Ba^{137m}$ logging method of the present invention will be used in conjunction with a cement bond log to efficiently identify channeling in newly cemented wellbores. For example, in many instances, it would be desirable to run a cement bond log of the entire segment of the well of interest. The cement bond log would be used to identify specific intervals which may have inadequate cementing. The present $Ba^{137m}$ logging method would then be performed over these intervals to determine whether the indications of inadequate cementing resulting from the cement bond log represent bypassed drilling fluid. This sequential logging is desirable in that the cement bond log can be performed at a considerably faster rate than the $Ba^{137m}$ log. Minimizing the length of the intervals to be logged for $Ba^{137m}$ results in a time savings.

The preferred method of practicing the present invention has been detailed above. It should be understood that the foregoing description is illustrative only and that other embodiments of the invention can be employed without departing from the full scope of the invention as set forth in the appended claims.

We claim:

1. A method for detecting barium bearing material in the annulus of a cased wellbore, comprising the steps of:
   introducing a population of neutrons into at least a portion of said wellbore, said neutrons having an initial mean energy in excess of 10 MeV;
   monitoring the activity level of Barium-137m observed within the wellbore as a function of depth;
   determining as a function of depth the activity level of Manganese-56 resulting from (n,p) reactions between said population of neutrons and said casing;
   normalizing the Barium-137m activity level based on changes in the Manganese-56 activity level; and
   recording the Barium-137m activity level as a function of depth.

2. A method for detecting the presence and quantity of barite weighted drilling fluid remaining in the cemented annulus of a cased wellbore, said method comprising the steps of:
   passing a neutron generator through the wellbore casing, said neutron generator being adapted to establish a population of neutrons having an initial mean energy in excess of 10 MeV;
   monitoring as a function of wellbore depth the activity level of Barium-137m;
   monitoring as a function of wellbore depth the activity level of Manganese-56;
   establishing a normalized Barium-137m activity level by multiplying the observed Barium-137m activity level by a factor inversely proportional to the observed Manganese-56 activity level; and
   establishing a graphical representation corresponding to the Barium-137m activity level as a function of depth.

3. The method as set forth in claim 2 wherein said monitoring step is performed by passing a gamma detector through said wellbore and recording as a function of depth the magnitude of the gamma photon peak centered at about 0.66 MeV.

4. The method as set forth in claim 2 wherein said normalized Barium-137m count rate is used in said graphical representation establishing step.

5. A method for examining a cased, cemented wellbore to identify any regions of bypassed drilling fluid within the cemented annulus of said wellbore, comprising the steps of:
   performing a sonic log of said wellbore to determine regions in which the amplitude of an induced sonic signal is anomalously high; and
   performing a Barium-137m log of such regions to determine whether such regions correspond to inclusions of barite weighted drilling fluid within said cemented annulus, said performance of a Barium-137m log including:
   passing a neutron source along at least a portion of one of said regions, said neutron source being adapted to release neutrons at energies in excess of 10 MeV; and monitoring and recording the activity level of Barium-137m as a function of depth, the presence of Barium-137m being indicative of the inclusion of barite-weighted drilling fluid within said cemented annulus;

monitoring as a function of depth the activity level of Manganese-56 resulting from neutron activation of the casing; and normalizing the Barium-137m activity level based on variations in the measured Manganese-56 activity level.

6. The method as set forth in claim 5, further including the step of displaying as a function of depth the activity level of Barium-137m.

* * * * *